US00PP11446P

United States Patent [19]

Jelenkovic et al.

[11] Patent Number: Plant 11,446

[45] Date of Patent: Jul. 18, 2000

[54] STRAWBERRY PLANT NAMED 'NJ8614-2'

[75] Inventors: Gojko L. Jelenkovic, Piscataway; Joseph A. Fiola, Whiting; Peter J. Nitzsche, Scotch Plains, all of N.J.

[73] Assignee: Rutgers University, New Brunswick, N.J.

[21] Appl. No.: 09/034,120

[22] Filed: Mar. 3, 1998

[51] Int. Cl.[7] ..... A01H 5/00

[52] U.S. Cl. ..... Plt./208

[58] Field of Search ..... Plt./208

[56] References Cited

U.S. PATENT DOCUMENTS

P.P. 5,268 8/1984 Bringhurst et al. ..... Plt./208

P.P. 8,535 1/1994 Musacchi et al. ..... Plt./208

*Primary Examiner*—Howard J. Locker
*Assistant Examiner*—Wendy P. Baker
*Attorney, Agent, or Firm*—Synnestvedt & Lechner LLP

[57] ABSTRACT

A new and distinct cultivar of strawberry plant (*Fragaria× ananassa*) named 'NJ8614-2', which is a short day cultivar similar to 'Earliglow', but which is exceptional for its disease resistance and its combination of early season harvest of very attractive large fruit, with high productivity. The plant is well adapted to matted-row, ribbon-row, and high density planting systems, and performs consistently in diverse environments. The fruit size is larger than that of 'Earliglow', the major cultivar in its season, and the fruit flavor is good.

3 Drawing Sheets

BACKGROUND OF THE NEW PLANT

The present invention relates to the discovery and asexual propagation of a new and distinct short day type cultivar of strawberry plant (*Fragaria×ananassa*) plant, which resulted from crossing the selection 'NYUS119' as the seed parent and the selection 'NJ7910-1' as the pollen parent in 1986 at the Rutgers University Plant Science Greenhouses in New Brunswick, N.J. Both parent plants are unpatented, non-commercial varieties. The complete pedigree of 'NJ8614-2' is shown below:

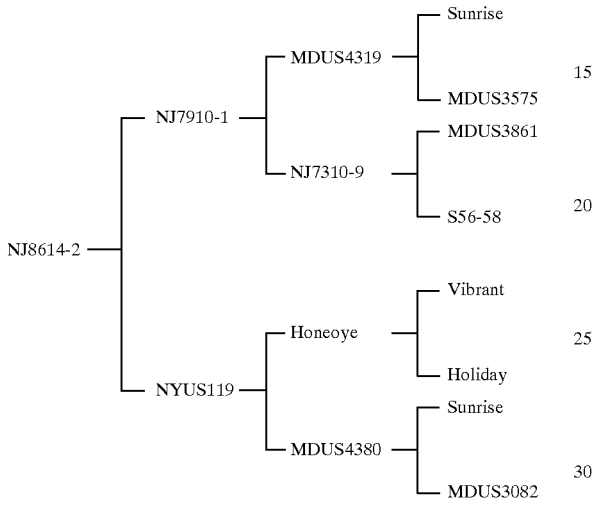

The new cultivar has been designated as 'NJ8614-2'. This specific clone was the second of seven selections in the progeny, and was discovered by Gojko L. Jelenkovic in June, 1988 at Rutgers Plant Science Farm 3 in New Brunswick, N.J. The new 'NJ8614-2' plant was recognized as being similar to the known (unpatented) 'Honeoye' variety with respect to its fruit and production, but distinguishable therefrom and from other known varieties in that it demonstrates multiple disease resistance.

The new plant was designated 'NJ8614-2' in the breeding records and was first asexually propagated, by runners, by Gojko L. Jelenkovic in about July, 1988 at Rutgers Plant Science Farm 3. It was recognized and selected as a distinctive and superior clone by Joseph A. Fiola based on extensive testing at the Rutgers Fruit Research and Extension Center in Cream Ridge, N.J.; and by Peter J. Nitzsche based on testing at the Snyder Research and Extension Center in Pittstown, N.J. Limited grower testing started in 1994. The new cultivar has shown to be stable in its distinguishing characteristics over several generations, through successive asexual propagations using runners.

DETAILED BOTANICAL DESCRIPTION OF THE NEW PLANT

Figure 1:
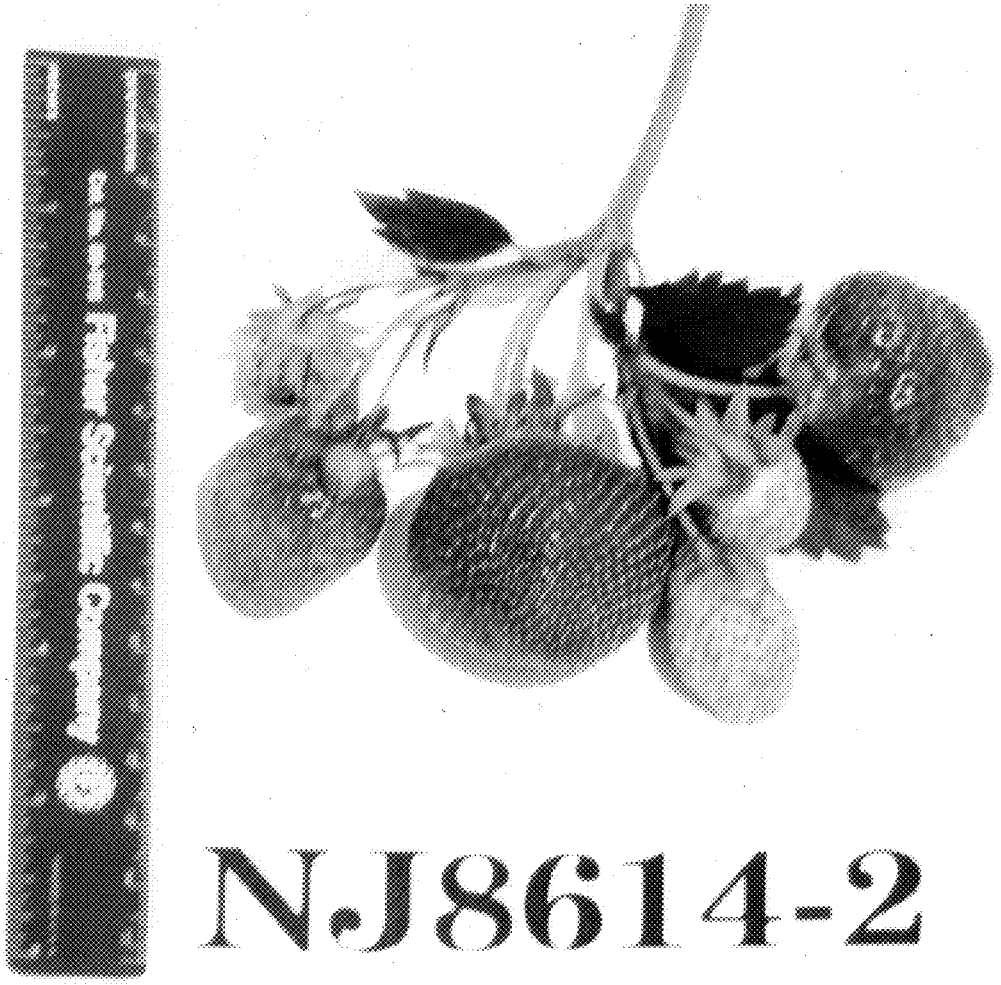
FIG. 1 depicts a raceme of the fruit of the new cultivar, with reference to a 6-inch (15 cm.) ruler.
Figure 2:
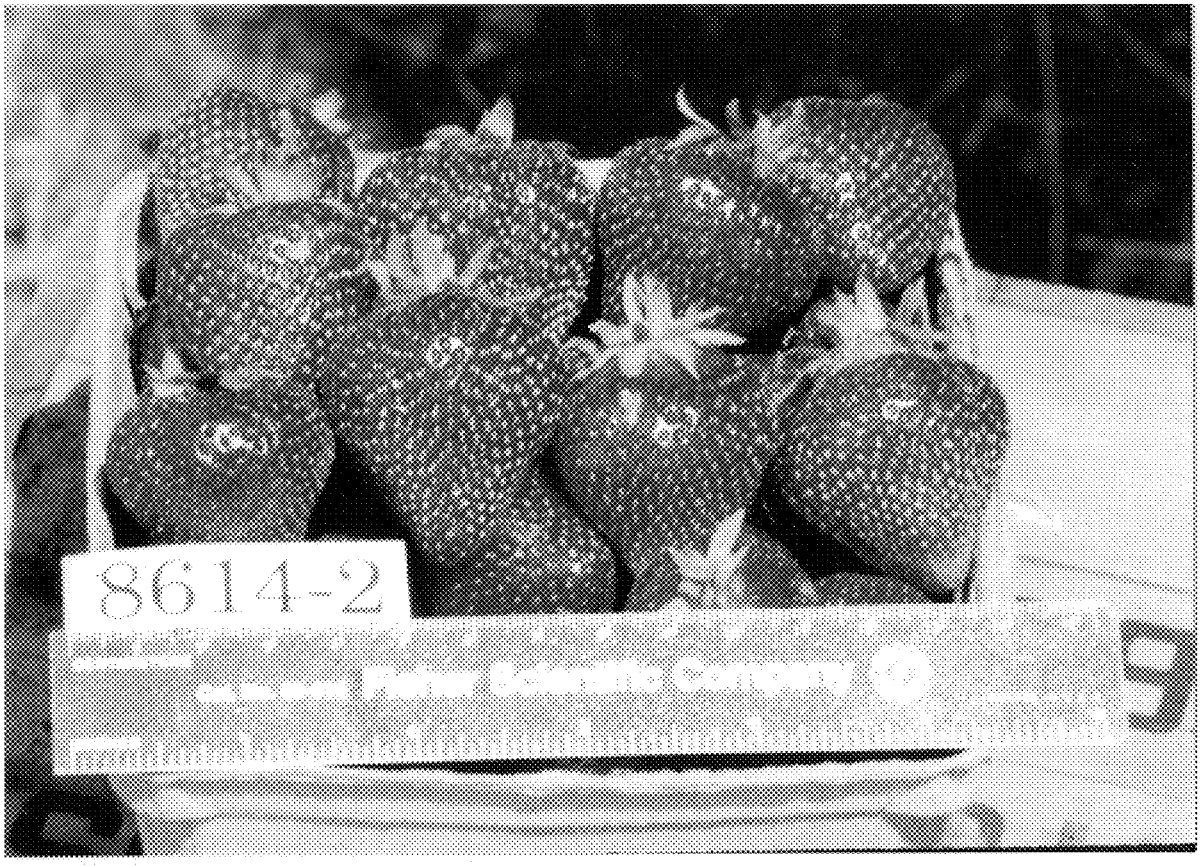
FIG. 2 illustrates a quart of primary fruits of the new cultivar, with reference to a 6-inch (15 cm.) ruler.
Figure 3:
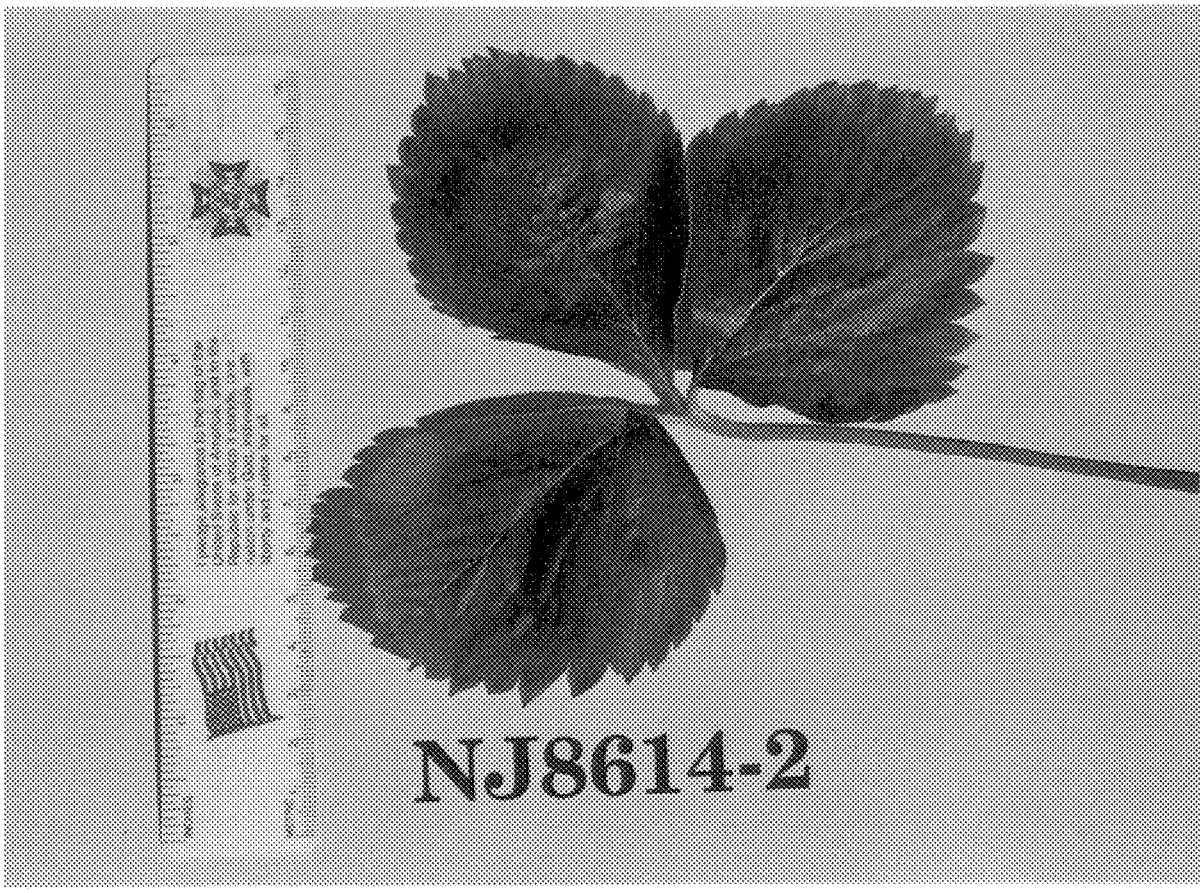
FIG. 3 illustrates a typical trifoliate leaf of the new cultivar, with reference to a 6-inch (15 cm.) Ruler.

The following detailed description of the new 'NJ8614-2' plant is based upon observations made of the plants grown in Cream Ridge, N.J., during about the months of May and June. It is believed that this description will apply to 'NJ8614-2' cultivar plants grown in similar conditions of soil and climate elsewhere.

Throughout this specification, color names beginning with a small letter signify that the name of that color as used in common speech is aptly descriptive. Color names beginning with a capital letter designate color values based on the R.H.S. Colour Chart published by The Royal Horticultural Society of London, England.

Plants and foliage: The vegetative habit of the new plant is one of medium overall vigor, with branching and runnering to form a moderate density matted-row. It produces few but large crowns when planted in high density on plastic. It is also well adapted to ribbon-row culture.

The new plant appears to be generally well adapted to, and has performed exceptionally well on, heavier soils in the northern locations of New Jersey.

The trifoliate leaves are semi-erect, petioles bearing lightly scattered hirsute hairs; 3 leaflets ovate-orbicular, margins serrate, apices round, bases of terminal leaflets cuneate and 2 lateral leaflet bases strongly oblique; upper leaflet surface lightly and scattered sericeous on and between the veins; lower leaflet surface lightly and scattered sericeous hairs on and between the veins; all leaflet hairs appressed; petiolules lightly hirsute. Adaxial and abaxial leaf surfaces are medium green in coloration and typical of the species. Typical measurements for the trifoliate leaves are shown in Table 6.

Isozymes in leaf extracts: Isozyme patterns for glucose phosphate isomerase (GPI), leucine amino peptidase (LAP), and phosphoglucomutase (PGM) show banding patterns for this genotype (Table 5).

Disease and pest reaction: The foliage has good leaf spot and powdery mildew resistance, and will tolerate leaf scorch. The plant has been screened for resistance against strains A-1, A-2, A-3, A-4, and A-6 of Phytophthora, which causes red stele. The plants have also shown good field resistance to Verticillium wilt.

Flowering fruit and production characteristics: The plant flowers over a short period with the majority of flowers opening about a few days later than the known (unpatented) 'Earliglow' variety, about the last week in April/first week in May. Flowers are white in coloration and typical of the species. Fruit are numerous, large, and borne on medium length trusses. In particular, the primary peduncle (range 60–100 mm) branches to a group of pedicels (range 25–60 mm) supporting the primaries, secondaries, tertiaries, etc.

The strawberry fruit is very attractive, brightly colored, with medium to high gloss. Primary fruit are very large, with secondary and tertiary fruit also maintaining good commercial size. The largest individual primaries of a harvest can weigh in excess of 40 grams/fruit. Seed are yellow to tan, typical of the species, and set flush or slightly raised above the berry surface. The fruit has a slight shoulder and the calyx is about 11.0 mm in diameter and is bright green, typical of the species, attractive and slightly reflexed.

The berry skin has good abrasion resistance and the flesh is firm. The berry color is bright red (Red 46A). Internal color is similar in hue and with slight gradation to lighter tones towards the center. The fruit has good sweet/acid balances, and medium to strong strawberry flavor intensity.

TABLE 1

Yield parameters of 'NJ8614-2', relative to other cultivars and selections of the early harvest season, in a matted-row production system at Cream Ridge, New Jersey; data is combined means of 1991 and 1992.

| | Plant | | Yield | | Berry Wt.** | |
|---|---|---|---|---|---|---|
| Genotype | Bed | Vig* | Early (lb/A) | Total (lb/A) | Prim*** (g) | Avg (g) |
| NJ8607-2 | 6 | 75 | 2170 | 10880 | 17.3 | 12.5 |
| NJ8608-1 | 7 | 55 | 1180 | 8720 | 16.4 | 13.8 |
| NJ8614-2 | 7 | 65 | 1060 | 10470 | 16.4 | 12.5 |

TABLE 1-continued

Yield parameters of 'NJ8614-2', relative to other cultivars and selections of the early harvest season, in a matted-row production system at Cream Ridge, New Jersey; data is combined means of 1991 and 1992.

| | Plant | | Yield | | Berry Wt.** | |
|---|---|---|---|---|---|---|
| Genotype | Bed | Vig* | Early (lb/A) | Total (lb/A) | Prim*** (g) | Avg (g) |
| Earliglow | 7 | 80 | 1390 | 11970 | 14.0 | 9.5 |
| Raritan | 6 | 85 | 610 | 11880 | 16.7 | 13.0 |

*Plant vigor ratings are determined through a rating of the vigor of the plant on a subjective scale of 10 (plant extremely weak) to 90 (plant strong, vigorous, filling in predetermined production area).
**Data obtained by weighing a random selection of 20 fruit from a plot at each harvest.
***Refers to the primary or first harvested berries.

TABLE 2

Yield parameters of 'NJ8614-2', relative to other cultivars and selections of the early harvest season, in a matted-row production system at Cream Ridge, New Jersey; data is combined means of 1994 and 1995.

| | Plant | | Yield | | Berry Wt.** | |
|---|---|---|---|---|---|---|
| Genotype | Bed | Vig* | Early (lb/A) | Total (lb/A) | Prim*** (g) | Avg (g) |
| NJ8607-2 | 6 | 75 | 1590 | 11046 | 16.5 | 12.2 |
| NJ8608-1 | 7 | 55 | 1350 | 8610 | 13.9 | 11.6 |
| NJ8614-2 | 7 | 65 | 1100 | 9170 | 16.3 | 12.9 |
| Earliglow | 7 | 80 | 2280 | 9400 | 11.8 | 9.6 |
| Annapolis | 6 | 85 | 740 | 5350 | 14.0 | 11.0 |

*Plant vigor ratings are determined through a rating of the vigor of the plant on a subjective scale of 10 (plant extremely weak) to 90 (plant strong, vigorous, filling in predetermined production area).
**Data obtained by weighing a random selection of 20 fruit from a plot at each harvest.
***Refers to the primary or first harvested berries.

TABLE 3

Yield parameters of 'NJ8614-2', relative to other cultivars and selections of the early harvest season, in a plasticulture system at Cream Ridge, New Jersey; data is combined means of 1994 and 1995.

| | | Yield | | Berry Wt.** | |
|---|---|---|---|---|---|
| Genotype | Plant Vig* | Early (lb/A) | Total (lb/A) | Prim*** (g) | Avg (g) |
| NJ8826-11 | 67 | 1440 | 6960 | 14.5 | 11.0 |
| NJ8607-2 | 65 | 660 | 6110 | 14.1 | 11.4 |
| NJ8606-1 | 63 | 760 | 6940 | 13.1 | 10.1 |
| NJ8614-2 | 65 | 740 | 7530 | 15.7 | 12.3 |
| Chandler | 79 | 330 | 9790 | 14.2 | 11.5 |

*Plant vigor ratings are determined through a rating of the vigor of the plant on a subjective scale of 10 (plant extremely weak) to 90 (plant strong, vigorous, filling in predetermined production area).
**Data obtained by weighing a random selection of 20 fruit from a plot at each harvest.
***Refers to the primary or first harvested berries.

TABLE 4

Mean berry length (L), width (W), and girth (G) for 'NJ8614-2' and other cultivars; data from 1995.

| Genotype | Length (mm) | Width (mm) | Girth (mm) |
|---|---|---|---|
| NJ8607-2 | 35 | 37 | 31 |
| NJ8826-11 | 40 | 47 | 40 |
| NJ8614-2 | 36 | 39 | 26 |
| NJ8608-1 | 43 | 37 | 33 |
| NJ8944-1 | 45 | 47 | 40 |
| Chandler | 37 | 35 | 28 |

TABLE 5

Isozymes patterns for leaf extracts for glucose phosphate isomerase (GPI), leucine amino peptidase (LAP), and phosphoglucomutase (PGM).

| Genotype | GPI | LAP | PGM |
|---|---|---|---|
| NJ8826-11 | A6 | B3 | C2 |
| NJ8614-2 | A1 | B3 | C3 |
| NJ8607-2 | A1 | B3 | C3 |
| Chandler | A1 | B3 | C1 |

TABLE 6

Typical measurements for length and width of trifoliate leaves of 'NJ8614-2'

| | 1° leaf | | 2° leaves | |
|---|---|---|---|---|
| | Length (mm) | Width (mm) | Length (mm) | Width (mm) |
| Average | 90 | 72 | 85 | 70 |
| Range: | | | | |
| high | 96 | 80 | 90 | 80 |
| low | 85 | 65 | 80 | 60 |

We claim:

1. A new and distinct strawberry plant named 'NJ8614-2', as herein illustrated and described.

* * * * *